(12) United States Patent  
Kao et al.

(10) Patent No.: US 8,512,233 B2  
(45) Date of Patent: Aug. 20, 2013

(54) CURVED LARYNGOSCOPE AND OPERATION INSTRUMENT ASSEMBLY APPLYING THE SAME

(75) Inventors: Yu-Jin Kao, Taipei County (TW); Hong-Wen Chang, Taipei County (TW); Chih-Wen Yang, Taoyuan County (TW); Shaw-Hwa Parng, Kaohsiung County (TW); Tzu-Yu Hsiao, Taipei (TW)

(73) Assignees: Industrial Technology Research Institute, Hsinchu (TW); National Taiwan University Hospital, Taipei (TW)

( * ) Notice: Subject to any disclaimer, the term of this patent is extended or adjusted under 35 U.S.C. 154(b) by 337 days.

(21) Appl. No.: 12/947,776

(22) Filed: Nov. 16, 2010

(65) Prior Publication Data

US 2012/0029292 A1 Feb. 2, 2012

(30) Foreign Application Priority Data

Jul. 27, 2010 (TW) .............................. 99124785 A

(51) Int. Cl.
*A61B 1/267* (2006.01)

(52) U.S. Cl.
USPC ......................................... 600/190; 600/188

(58) Field of Classification Search
USPC ................. 600/185, 187, 188, 190, 194, 211, 600/221
See application file for complete search history.

(56) References Cited

U.S. PATENT DOCUMENTS

| 4,337,761 | A |   | 7/1982  | Upsher |
| 4,905,669 | A | * | 3/1990  | Bullard et al. ................ 600/104 |
| 5,676,635 | A |   | 10/1997 | Levin |
| 5,800,344 | A |   | 9/1998  | Wood, Sr. et al. |
| 6,890,298 | B2 |  | 5/2005  | Berci et al. |
| 7,648,457 | B2 |  | 1/2010  | Stefanchik et al. |

FOREIGN PATENT DOCUMENTS

WO 2009007478 1/2009

OTHER PUBLICATIONS

"Office Action of Taiwan Counterpart Application", issued on Nov. 16, 2012, p. 1-p. 4.

* cited by examiner

*Primary Examiner* — Andrew Yang
(74) *Attorney, Agent, or Firm* — Jianq Chyun IP Office

(57) ABSTRACT

A curved laryngoscope and an operation instrument assembly applying the same are provided, wherein the curved laryngoscope is provided with a guiding structure and a locating device. The guiding structure and the locating device can be individually or both adopted in the curved laryngoscope to assist various operation instruments in moving and being located reliably, and therefore improve the reliability, accuracy and facility in operation using the curved laryngoscope.

22 Claims, 6 Drawing Sheets

A-A'

A-A'

A-A'

B-B'

US 8,512,233 B2

CURVED LARYNGOSCOPE AND OPERATION INSTRUMENT ASSEMBLY APPLYING THE SAME

CROSS REFERENCE TO RELATED APPLICATIONS

This application claims the priority benefit of Taiwan application serial no. 99124785, filed on Jul. 27, 2010. The entirety of the above-mentioned patent application is hereby incorporated by reference herein and made a part of this specification.

TECHNICAL FIELD

The disclosure is related to a laryngoscope, and more particularly, to a curved laryngoscope and operation instrument assembly applying the same.

BACKGROUND

Laryngoscopes belong to a type of deep throat operation instrument, which is a straight hollow tube shape instrument. When operating, the whole body of the patient must be anesthetized, and the head of the patient must face upward, so the neck portion is in a straight position. The laryngoscope enters via the oral cavity to go deep into the throat, directly to the operation location. The function of the hollow tube in the laryngoscope is to provide enough space to let a normal microsurgery instrument and video instrument arrive at the operation region of the deep portion of the throat and carry out an operation.

However, since most laryngoscopes today are straight structures, during operation, the patient is easily injured at the oral cavity and neck, forming what is called a second degree injury. A curved laryngoscope can attempt to conform to the human body throat curves, and operate with related curved operation instruments and video instruments, to alter conventional surgery operating modes, and lessen the second degree injuries of currently operated patients. However, when actually using the curved laryngoscope, the operation instrument and the video instrument need to move along the curves of the laryngoscope. Because it is visually impossible to steadily look at and impossible to instinctively feel the nature of the operation, it is hard to control the position of the operation instrument and the video instrument in the curved laryngoscope, which in turn affects the surgical operation reliability, accuracy and facility.

SUMMARY

The disclosure provides a curved laryngoscope, for improving the reliability, accuracy and facility of operation instruments and video instruments.

The disclosure provides an operation instrument assembly of the curved laryngoscope, which has good reliability, accuracy and facility in operation.

The disclosure addresses a curved laryngoscope, suitable for combining with an operation instrument. The curved laryngoscope of the disclosure includes a curved hollow tube and a locating device. The hollow tube comprises a first end and a second end. During operation, the second end of the hollow tube enters the patient. An inner wall of the hollow tube has a guiding structure. The operation instrument enters the hollow tube by extending through the first end, and protrudes out the hollow tube through the second end. The operation instrument utilizes the guiding structure to mate with the inner wall of the hollow tube, so as to slide along the inner wall. The locating device is disposed in the hollow tube. The locating device clamps the operation instrument, so as to position the operation instrument at a specific location of a section of the hollow tube.

Applying the design of the curved laryngoscope, the disclosure further addresses an operation instrument assembly, comprising a curved hollow tube, an operation instrument, and a locating device. The curved hollow tube comprises a first end and a second end. During operation, the second end of the hollow tube enters the patient. An inner wall of the hollow tube has a guiding structure. The operation instrument enters the hollow tube by extending through the first end, and protrudes out the hollow tube through the second end. The operation instrument utilizes the guiding structure to mate with the inner wall of the hollow tube, so as to slide along the inner wall. The locating device is disposed in the hollow tube. The locating device clamps the operation instrument, so as to position the operation instrument at a specific location of a section of the hollow tube.

The disclosure addresses another curved laryngoscope, suitable for combining with an operation instrument. The curved laryngoscope includes a curved hollow tube and a locating device. The hollow tube comprises a first end and a second end. During operation, the second end of the hollow tube enters the patient. The operation instrument enters the hollow tube by extending through the first end, and protrudes out the hollow tube through the second end. The locating device is disposed in the hollow tube. The locating device clamps the operation instrument, so as to position the operation instrument at a specific location of a section of the hollow tube.

Applying the design of the other curved laryngoscope, the disclosure further addresses an operation instrument assembly, comprising a curved hollow tube, an operation instrument, and a locating device. The hollow tube comprises a first end and a second end. During operation, the second end of the hollow tube enters the patient. The operation instrument enters the hollow tube by extending through the first end, and protrudes out the hollow tube through the second end. The locating device is disposed in the hollow tube. The locating device clamps the operation instrument, so as to position the operation instrument at a specific location of a section of the hollow tube.

The disclosure addresses yet another curved laryngoscope, suitable for combining with an operation instrument. The curved laryngoscope includes a curved hollow tube, an independent channel, and a locating device. The hollow tube comprises a first end and a second end. During operation, the second end of the hollow tube enters the patient. An inner wall of the hollow tube has a guiding structure. The operation instrument enters the hollow tube by extending through the first end, and protrudes out the hollow tube through the second end. The operation instrument utilizes the guiding structure to mate with the inner wall of the hollow tube, so as to slide along the inner wall. The independent channel is integrally formed with the inner wall of the hollow tube, and the independent channel is separated from the remaining space in the hollow tube. A video instrument is disposed in the independent channel. The locating device is disposed in the hollow tube, and the locating device comprises of a securing ring, a plurality of pins, and a plurality of elastic elements. The securing ring is disposed in the inner wall of the hollow tube. The securing ring comprises a first opening for the operation instrument to pass through and a second opening for the video instrument to pass through. The plurality of pins is disposed on the securing ring, and protrudes through the first opening.

The plurality of elastic elements are respectively disposed between the plurality of pins and the securing ring, so as to drive the pins to collectively lean against the operation instrument.

Applying the design of the yet another curved laryngoscope, the disclosure further addresses an operation instrument assembly, comprising a curved hollow tube, an independent channel, an operation instrument, a video instrument, and a locating device. The curved hollow tube comprises a first end and a second end. During operation, the second end of the hollow tube enters the patient. An inner wall of the hollow tube has a guiding structure. The independent channel is integrally formed with the inner wall of the hollow tube, and the independent channel is separated from the remaining space in the hollow tube. The operation instrument enters the hollow tube by extending through the first end, and protrudes out the hollow tube through the second end. The operation instrument utilizes the guiding structure to mate with the inner wall of the hollow tube, so as to slide along the inner wall. A video instrument is disposed in the independent channel. The locating device is disposed in the hollow tube. The locating device comprises of a securing ring, a plurality of pins, and a plurality of elastic elements. The securing ring is disposed in the inner wall of the hollow tube. The securing ring comprises a first opening for the operation instrument to pass through and a second opening for the video instrument to pass through. The plurality of pins is disposed on the securing ring, and protrudes through the first opening. The plurality of elastic elements are respectively disposed between the plurality of pins and the hollow tube, so as to drive the plurality of pins to collectively lean against the operation instrument.

Because of the aforementioned, the disclosure disposes a guiding structure or a locating device that can assist in the movement reliability and positioning reliability of the operation instrument in the inner wall of the hollow tube of the curved laryngoscope. Thus, there is an improvement in the reliability, accuracy and facility of the operation instrument (including the video instrument) when in operation using the curved laryngoscope.

Several exemplary embodiments accompanied with figures are described in detail below to further describe the disclosure in details.

BRIEF DESCRIPTION OF THE DRAWINGS

The accompanying drawings are included to provide a further understanding of the disclosure, and are incorporated in and constitute a part of this specification. The drawings illustrate embodiments of the disclosure and, together with the description, serve to explain the principles of the disclosure.

DESCRIPTION OF EMBODIMENTS

The inner wall of the curved laryngoscope addressed in the disclosure comprises an assisting structure, so as to assist the movement and placement of an operation instrument. This resolves the issue of shaky and unsteady movement during surgery caused by the discrepancy between instinctive tactile sensing and watching a video when operating. It allows the user (such as a doctor) to use the operation instrument to cut, clamp, clip, slice with more precision, increasing the operation reliability, operation accuracy, and operation facility, substantially reducing the risk and time of surgery. In particular, the curved laryngoscope of the disclosure aids in increasing the success rate of deep throat surgery. It also applies to minimal invasive surgery in deep areas of other body tissues, and has industry value in medical appliances.

Figure 1:
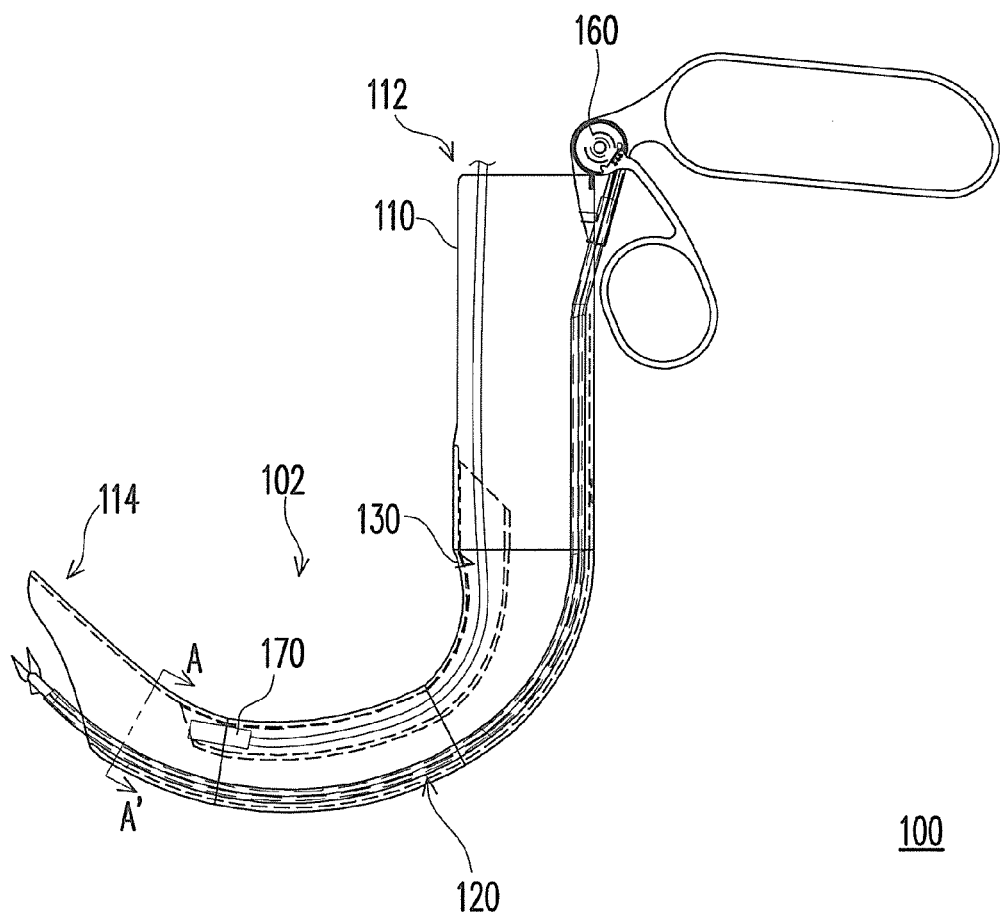
FIG. 1 is a schematic side view of an operation instrument assembly according to an embodiment of the disclosure.

FIG. 1 is a schematic side view of an operation instrument assembly according to an embodiment of the disclosure. As shown in FIG. 1, the operation instrument assembly 100 of the embodiment directs to an assembly of the combination of a curved laryngoscope 102 and an operation instrument 160. The curved laryngoscope 102 can actually exist independently, but for the sake of simplicity, the embodiment describes the assembled structure of the combination of the curved laryngoscope 102 and the operation instrument 160.

The curved laryngoscope 102 includes a curved hollow tube 110, wherein the hollow tube 110 comprises a first end 112 and a second end 114. In the embodiment, the curve angle of the hollow tube 110 ranges between 90° and 180°. The curve range is directed to the curve angle from the first end 112 to the second end 114 of the hollow tube 110, wherein at least one curve (or an R angle) exists. Of course, the quantity or angle range of the R angle is adjusted according to the actual need. In other embodiments, the curve angle of the hollow tube 110 can range between 0° and 180°.

During surgery, the hollow tube 110 enters the patient body through the second end 114, utilizing the curvature range of the hollow tube 110 to conform to the curvature of the body's throat. Thus, during the operation, injuries to the oral cavity and neck of the patient can be avoided, keeping away from what is called a second degree injury.

Figure 2:
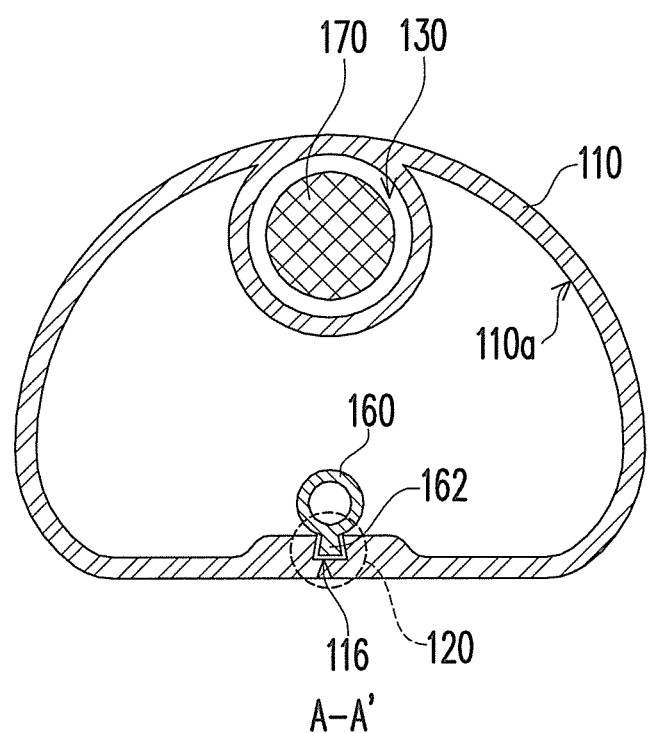
FIG. 2 is a cross-sectional view of the structure in FIG. 1 along section A-A'.

FIG. 2 further shows a cross-sectional view of the structure in FIG. 1 along section A-A'. Please refer to FIG. 1 and FIG. 2. The inner wall 110a of the hollow tube 110 of the embodiment comprises a guiding structure 120. It is used to assist the movement and placement of the operation instrument 160 within the hollow tube 110. More specifically, the operation instrument 160 enters the hollow tube 110 by extending through the first end 112, and protrudes out the hollow tube 110 through the second end 114. The operation instrument 160 utilizes the guiding structure 120 to mate with the inner wall 110a of the hollow tube 110, so as to slide along the inner wall 110a.

When operating, the operation instrument 160 is inserted into the hollow tube 110 from the first end 112. With the assistance of the guiding structure 120, the operation instrument 160 slides along the inner wall 110a of the hollow tube 110. Then, the operation instrument 160 is pushed until the second end 114 of the hollow tube 110, and protrudes out of the hollow tube 110, to proceed with operating actions such as cutting, clamping, clipping, and slicing. In addition, the mentioned operation instrument 160 in the embodiment is not limited to scalpels, scissors, clamps, or other instruments, but includes other equipment applied during surgery such as endoscopes, illuminating light sources, and video devices. In other words, the disclosure also allows the guiding structure 120 to be applied to other types of operation instruments and curved laryngoscopes, and achieve similar effects.

In the embodiment, the guiding structure 120 and the operation instrument 160 operate in coordination through, for example, a sliding trough 116 and a sliding block 162. As shown in FIG. 2, the guiding structure 120 is, for instance, fabricated in the sliding trough 116 in the inner wall 110a of the hollow tube 110, and on the operation instrument 160 there is the sliding block 162 that mates with the sliding trough 116. The sliding block 162 slides within the sliding trough 116, so as to drive the operation instrument 160 to slide along the inner wall 110a of the hollow tube 110. The sliding trough 116 and the sliding block 162 of the embodiment are mated through, for example, a dovetail (wedge shape). The sliding trough 116 acts as the dovetail slot, and the sliding block 162 acts as the dovetail key.

Figure 3A:
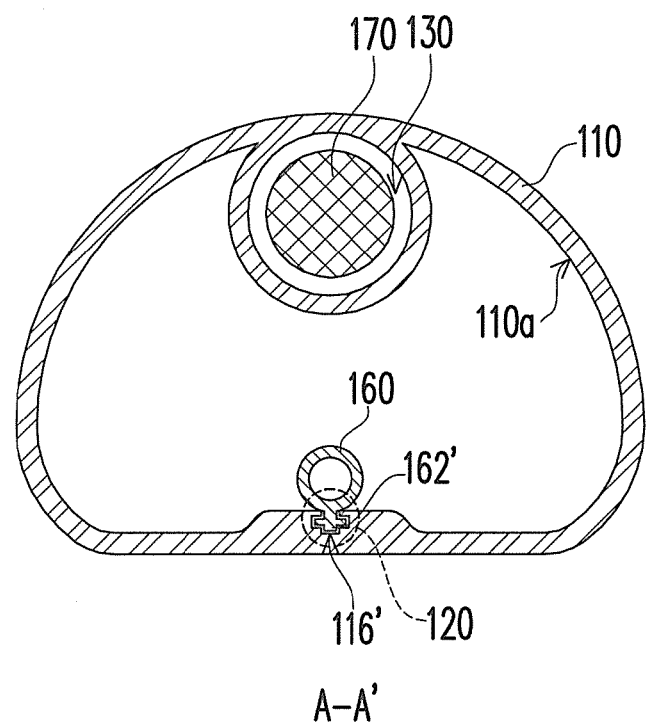
FIGS. 3A-3C are schematic cross-sectional views of the operation instrument assembly with three other types of different guiding structure designs, respectively.
Figure 3B:
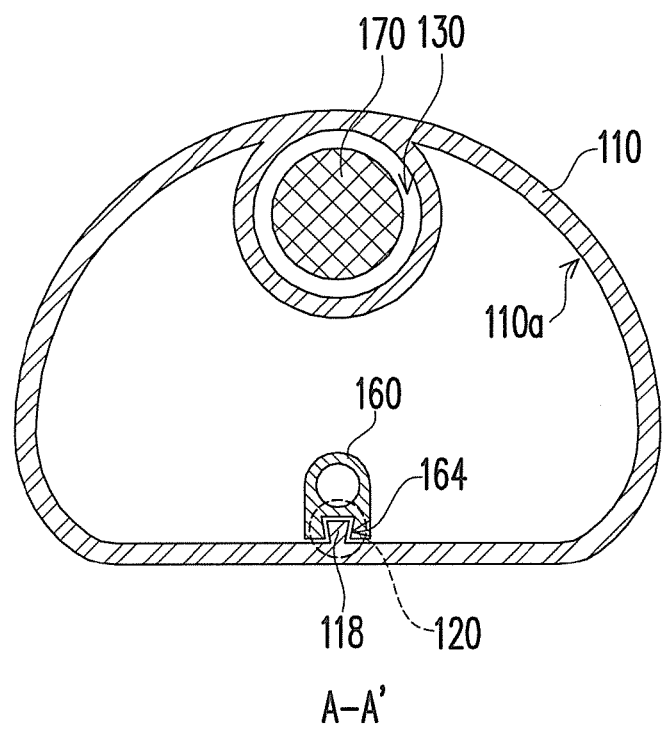
Figure 3C:
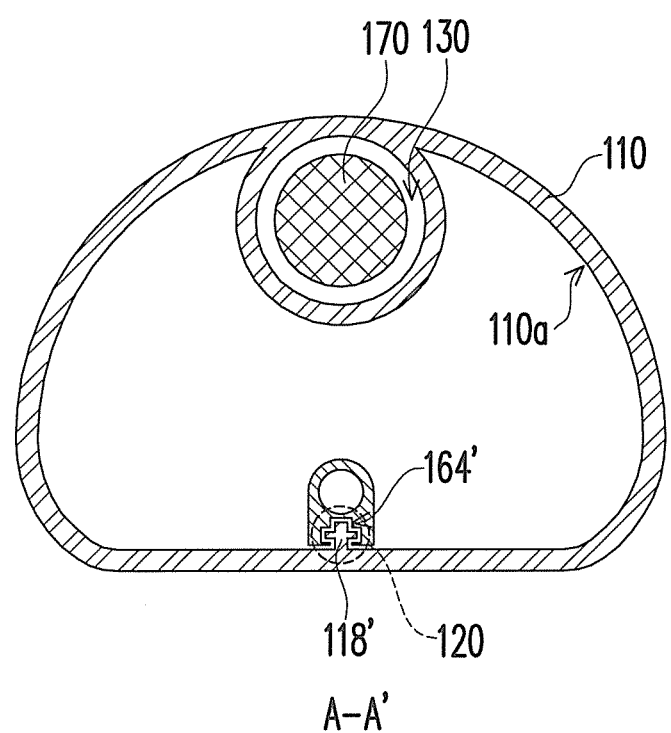

In other embodiments, the guiding structure 120 and the operation instrument 160 can be mated through other designs. FIGS. 3A-3C are schematic cross-sectional views of the operation instrument assembly with the three other types of different guiding structure designs, respectively. For explanation convenience, FIGS. 3A-3C adopts similar component references from FIG. 2, and only the differences will be explained.

First off, the guiding structure 120 shown in FIG. 3A is fabricated in the sliding trough 116' in the inner wall 110a of the hollow tube 110, and on the operation instrument 160 there is a sliding block 162' that mates with the sliding trough 116. The differences between the structures of FIG. 3A and FIG. 2 lie in the external shapes of the sliding trough 116' and sliding block 162' in FIG. 3A and the sliding trough 116 and sliding block 162 of FIG. 2.

In addition, the guiding structure 120 shown in FIG. 3B is fabricated in the sliding block 118 in the inner wall 110a of the hollow tube 110, and on the operation instrument 160 there is a sliding trough 164 that mates with the sliding block 118. The sliding block 118 and the sliding trough 164 are mated through, for example, a dovetail (wedge shape). The sliding block 118 acts as the dovetail key, and the sliding trough 164 acts as the dovetail slot.

Furthermore, the guiding structure 120 shown in FIG. 3C is fabricated in the sliding block 118' in the inner wall 110a of the hollow tube 110, and on the operation instrument 160 there is a sliding trough 164' that mates with the sliding block 118. The differences between the structures of FIG. 3C and FIG. 3B lie in the external shapes of the sliding block 118' and sliding trough 164' in FIG. 3C and the sliding block 118 and sliding trough 164 of FIG. 3B.

Of course, besides the designs mentioned in FIG. 2 and FIGS. 3A-3C, the guiding structure and operation instrument of the disclosure can use other feasible designs to achieve similar effects. What follows will not include anymore unnecessary details.

Please refer to FIGS. 1, 2, and 3A-3C. The curved laryngoscope 102 of the disclosure can be configured with a type of the mentioned operation instrument. In order to combine the hollow tube 110 of the curved laryngoscope 102 with a plurality of operation instruments, not only can the disclosure choose to increase the quantity of the guiding structure 120 in the inner wall 110a of the hollow tube 110, but can also form an independent channel 130 in the curved laryngoscope 102 within the hollow tube 110 such as those shown in FIGS. 1, 2, and 3A-3C. The independent channel 130, for instance, is formed as one with the hollow tube 110, and is integrally formed with the inner wall 110a of the hollow tube 110. The space that the independent channel 130 surrounds is separated from the remaining space in the hollow tube 110. A video instrument 170 is disposed in the independent channel 130 of the embodiment, which includes a charge-coupled device (CCD). The video instrument 170 enters the hollow tube 110 by extending through the first end 112, and follows along the independent channel 130 to reach the second end 114 of the hollow tube 110. The video instrument 170 can also be replaced with other operation instruments.

Figure 4:
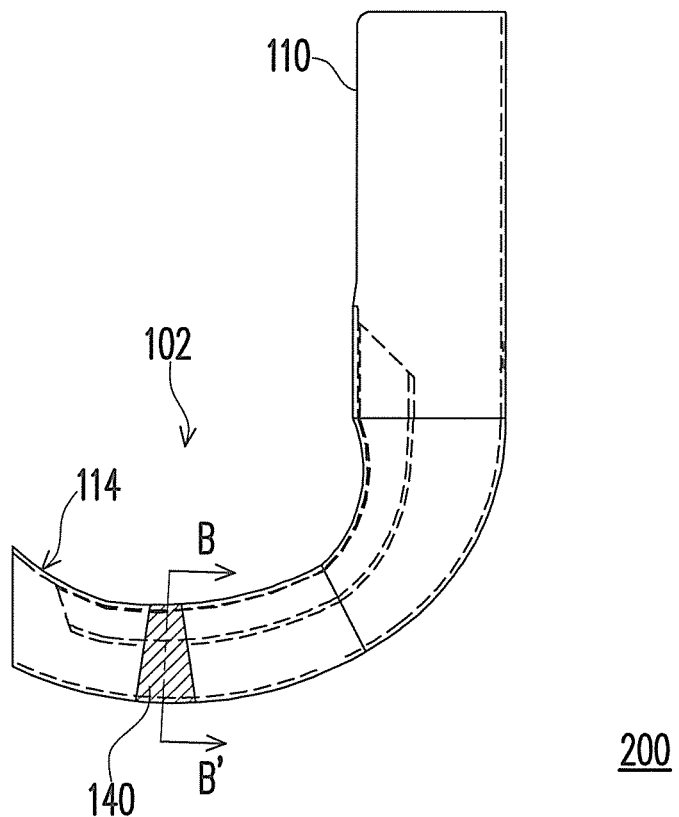
FIG. 4 is a schematic side view of an operation instrument assembly according to another embodiment of the disclosure.

FIG. 4 is a schematic side view of an operation instrument assembly according to another embodiment of the disclosure. An operation instrument assembly 200 of the embodiment can have similar structures with the operation instrument assembly 100 of the previous embodiment, thus the embodiment adopts similar component references from the previous embodiment. In addition, for the sake of clarity regarding the figures, the operation instrument 160 and the video instrument 170 were not drawn in FIG. 4. The guiding structure 120 of the previous embodiment may also exist in the embodiment.

As shown in FIG. 4, besides the guiding structure 120 of the previous embodiment, in order to steady the position of the operation instrument 160 in the hollow tube 110, and also ensure the operating reliability and accuracy, the curved laryngoscope 102 of the operation instrument assembly 200 of the embodiment includes a locating device 140. The locating device 140 is disposed in the hollow tube 110, and, for instance, is close to the second end 114 of the hollow tube 110. The locating device 140 clamps the operation instrument 160, so as to position the operation instrument 160 at a specific location of a section (such as section B-B') of the hollow tube 110. It should be noted that, even though the embodiment only shows a locating device 140, in reality, the locating device 140 of the embodiment can exist simultaneously with the guiding structure 120 of the previous embodiment. In other words, the curved laryngoscope of the disclosure can simultaneously adopt the guiding structure 120 of the previous embodiment and the locating device 140 of the embodiment to assist in the movement and placement of the operation instrument 160 and the video instrument 170. The embodiment only explains the detailed structure and function of the locating device 140.

Figure 5:
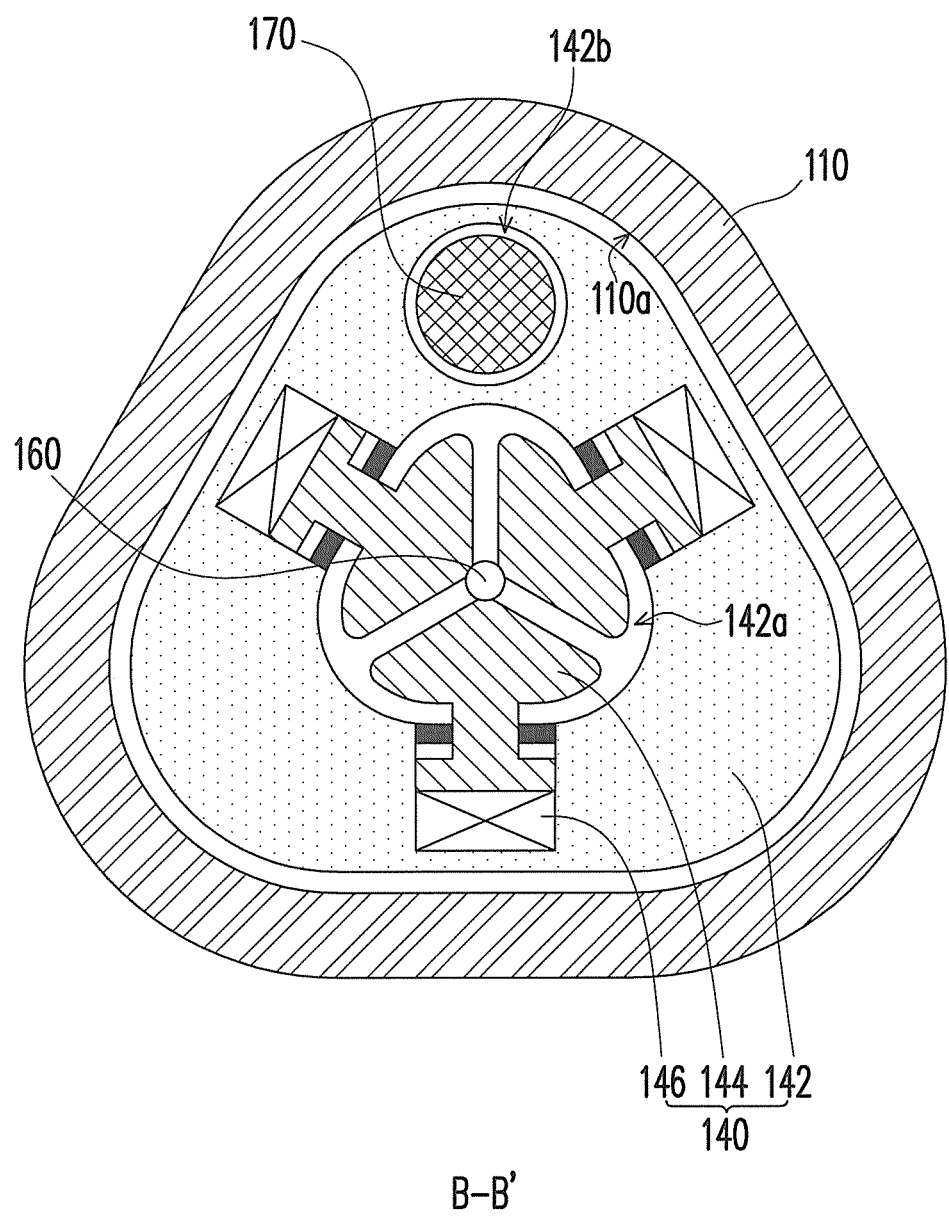
FIG. 5 is a cross-sectional view of the structure in FIG. 4 along section B-B'.

FIG. 5 is a cross-sectional view of the structure in FIG. 4 along section B-B'. The locating device 140 of the embodiment comprises a securing ring 142, a plurality of pins 144, and a plurality of elastic elements 146. The securing ring 142 is disposed in the inner wall 110a of the hollow tube 110. The securing ring 142 and the inner wall 110a of the hollow tube 110 can be joined using a slide track and slide block method to achieve mutual interference between the structures, the two can also be joined with other methods which include welding or adhering. The external shape of the securing ring 142 can be adjusted to the shape of a section of the hollow tube 110. In addition, the securing ring 142 comprises a first opening 142a for the operation instrument 160 to pass through and a second opening 142b for the video instrument 170 to pass through. The plurality of pins 144 is slidably disposed on the securing ring 142, and protrudes through the first opening 142a. The plurality of elastic elements 146 are respectively disposed between the plurality of pins 144 and the securing ring 142, so as to drive the pins 144 to collectively lean against the operation instrument 160. In the embodiment, the elastic joint 146 is, for example, a helical spring.

When the operation instrument 160 passes through the hollow tube 110, and reaches the locating device 140, the pins 144 press against the operation instrument 160 because of the force in the elastic elements 146, causing the operation instrument 160 to be positioned at a specific location on section B-B'. Herein, the clamping force of the locating device 140 with regard to the operation instrument 160 can be adjusted to suitable elastic elements, for example, selecting a spring with a suitable elastic force coefficient.

Even though the embodiment only shows one locating device 140, the other embodiments of the disclosure can choose to simultaneously dispose a plurality of locating devices 140 to provide assistance with the movement and placement of the operation instrument 160 and the video instrument 170. Thus, the operation instrument 160 and the video instrument 170 will respectively pass through a plurality of first openings 142a and second openings 142b in the securing rings 142 of the locating devices 140. The pins 144 of each locating device 140 collectively lean against the operation instrument 160. In addition, each component of the locating device 140 selectively uses material that can be compatible to biological organisms, and can include high temperature high pressure sterilization characteristics.

Generally, the disclosure addresses a curved laryngoscope provided with a guiding structure and a locating device, and also addresses the operation instrument assembly combined with the curved laryngoscope. The guiding structure and the locating device can be individually or both adopted in the curved laryngoscope to assist various operation instruments in moving and being located reliably, and therefore improve reliability, accuracy and facility in operation when using the curved laryngoscope.

It will be apparent to those skilled in the art that various modifications and variations can be made to the structure of the disclosed embodiments without departing from the scope or spirit of the disclosure. In view of the foregoing, it is intended that the disclosure cover modifications and variations of this disclosure provided they fall within the scope of the following claims and their equivalents.

What is claimed is:

1. A curved laryngoscope, suitable for combining with an operation instrument, the curved laryngoscope comprising:
   a curved hollow tube, comprising a first end and a second end, wherein an inner wall of the hollow tube includes a guiding structure, the operation instrument is adapted to enter the hollow tube by extending through the first end, and protrudes out the hollow tube through the second end, and the operation instrument is adapted to be assembled onto the inner wall of the hollow tube through the guiding structure to slide along the inner wall; and
   a locating device, disposed in the hollow tube, wherein the locating device is adapted to clamp the operation instrument to position the operation instrument at a specific location of a section of the hollow tube, the locating device comprising:
      a plurality of pins, disposed in the hollow tube, and the pins being adapted to collectively lean against the operation instrument; and
      a plurality of elastic elements, respectively disposed between the pins and the hollow tube, to provide an elastic force for the pins to lean against the operation instrument.

2. The curved laryngoscope of claim 1, wherein the guiding structure comprises a sliding trough, the sliding trough mates with a sliding block on the operation instrument.

3. The curved laryngoscope of claim 2, wherein the sliding trough and the sliding block mate through a dovetail.

4. The curved laryngoscope of claim 1, wherein the guiding structure comprises a sliding block, the sliding block mates with a sliding trough on the operation instrument.

5. The curved laryngoscope of claim 4, wherein the sliding trough and the sliding block mate through a dovetail.

6. The curved laryngoscope of claim 1, wherein the locating device further comprises:
   a securing ring, disposed in the hollow tube, the securing ring comprises an opening for the operation instrument to pass through, the pins are disposed on the securing ring and protrude through the opening, and the elastic elements are respectively disposed between the pins and the securing ring, so as to drive the pins to collectively lean against the operation instrument.

7. The curved laryngoscope of claim 1, further comprising:
   an independent channel, integrally formed with the inner wall of the hollow tube, and the independent channel is separated from the remaining space in the hollow tube, for containing a video instrument.

8. An operation instrument assembly, comprising:
   a curved hollow tube, comprising a first end and a second end, wherein an inner wall of the hollow tube includes a guiding structure;
   an operation instrument, entering the hollow tube by extending through the first end, and protruding out the hollow tube through the second end, wherein the operation instrument is assembled with the inner wall of the hollow tube through the guiding structure to slide along the inner wall; and
   a locating device, disposed in the hollow tube, wherein the locating device clamps the operation instrument to position the operation instrument at a specific location of a section of the hollow tube, the locating device comprising:
      a plurality of pins, disposed in the hollow tube, and the pins collectively lean against the operation instrument; and
      a plurality of elastic elements, respectively disposed between the pins and the hollow tube, to provide an elastic force for the pins to lean against the operation instrument.

9. The operation instrument assembly of claim 8, wherein the guiding structure comprises a sliding trough, the sliding trough mates with a sliding block on the operation instrument.

10. The operation instrument of claim 9, wherein the sliding trough and the sliding block mate through a dovetail.

11. The operation instrument assembly of claim 8, wherein the guiding structure comprises a sliding block, the sliding block mates with a sliding trough on the operation instrument.

12. The operation instrument of claim 11, wherein the sliding trough and the sliding block mate through a dovetail.

13. The operation instrument assembly of claim 8, wherein the locating device further comprises:
   a securing ring, disposed in the hollow tube, the securing ring comprises an opening for the operation instrument to pass through, the pins are disposed on the securing ring and protrude through the opening, and the elastic elements are respectively disposed between the pins and the securing ring, so as to drive the pins to collectively lean against the operation instrument.

14. The operation instrument assembly of claim 8, further comprising:
   an independent channel, integrally formed with the inner wall of the hollow tube, and the independent channel is separated from the remaining space in the hollow tube, for containing a video instrument.

15. A curved laryngoscope, suitable for combining with an operation instrument, the curved laryngoscope comprising:
   a curved hollow tube, comprising a first end and a second end, wherein the operation instrument is adapted to enter the hollow tube by extending through the first end, and protrudes out the hollow tube through the second end; and
   a locating device, disposed in the hollow tube, wherein the locating device is adapted to clamp the operation instrument to position the operation instrument at a specific location of a section of the hollow tube, the locating device comprising:

a plurality of pins, disposed in the hollow tube, and the pins being adapted to collectively lean against the operation instrument; and a plurality of elastic elements, respectively disposed between the pins and the hollow tube, to provide an elastic force for the pins to lean against the operation instrument.

16. The curved laryngoscope of claim 15, wherein the locating device further comprises:

a securing ring, disposed in the hollow tube, the securing ring comprises an opening for the operation instrument to pass through, the pins are disposed on the securing ring and protrude through the opening, and the elastic elements are respectively disposed between the pins and the securing ring, so as to drive the pins to collectively lean against the operation instrument.

17. The curved laryngoscope of claim 15, further comprising:

an independent channel, integrally formed with the inner wall of the hollow tube, and the independent channel is separated from the remaining space in the hollow tube, for containing a video instrument.

18. An operation instrument assembly, comprising:

a curved hollow tube, comprising a first end and a second end;

an operation instrument, entering the hollow tube by extending through the first end, and protruding out the hollow tube through the second end; and a locating device, disposed in the hollow tube, wherein the locating device clamps the operation instrument to position the operation instrument at a specific location of a section of the hollow tube, the locating device comprising:

a plurality of pins, disposed in the hollow tube, and the pins collectively lean against the operation instrument; and a plurality of elastic elements, respectively disposed between the pins and the hollow tube, to provide an elastic force for the pins to lean against the operation instrument.

19. The operation instrument assembly of claim 18, wherein the locating device further comprises:

a securing ring, disposed in the hollow tube, the securing ring comprises an opening for the operation instrument to pass through, the pins are disposed on the securing ring and protrude through the opening, and the elastic elements are respectively disposed between the pins and the securing ring, so as to drive the pins to collectively lean against the operation instrument.

20. The operation instrument assembly of claim 18, further comprising:

an independent channel, integrally formed with the inner wall of the hollow tube, and the independent channel is separated from the remaining space in the hollow tube, for containing a video instrument.

21. A curved laryngoscope, suitable for combining with an operation instrument and a video instrument, the curved laryngoscope comprising:

a curved hollow tube, comprising a first end and a second end, wherein an inner wall of the hollow tube includes a guiding structure, the operation instrument is adapted to enter the hollow tube by extending through the first end, and protrudes out the hollow tube through the second end, the operation, instrument is adapted to be assembled with the inner wall of the hollow tube through the guiding structure to slide along the inner wall;

an independent channel, integrally formed with the inner wall of the hollow tube, wherein the independent channel is separated from the remaining space in the hollow tube, and the video instrument is adapted to be disposed within the independent channel; and a locating device, disposed in the hollow tube, the locating device comprising:

a securing ring, disposed in inner wall of the hollow tube, wherein the securing ring comprises a first opening for the operation instrument to pass through and a second opening for the video instrument to pass through;

a plurality of pins, disposed on the securing ring, and protruding through the first opening; and a plurality of elastic elements, respectively disposed between the pins and the securing ring, so as to drive the pins to collectively lean against the operation instrument.

22. An operation instrument assembly, comprising:

a curved hollow tube, comprising a first end and a second end, wherein an inner wall of the hollow tube includes a guiding structure;

an independent channel, integrally formed with the inner wall of the hollow tube, wherein the independent channel is separated from the remaining space in the hollow tube;

an operation instrument, entering the hollow tube by extending through the first end, and protruding out the hollow tube through the second end, wherein the operation instrument is assembled with the inner wall of the hollow tube through the guiding structure to slide along the inner wall;

a video instrument, disposed in the independent channel; and a locating device, disposed in the hollow tube, the locating device comprising:

a securing ring, disposed in the hollow tube, wherein the securing ring comprises a first opening for the operation instrument to pass through and a second opening for the video instrument to pass through;

a plurality of pins, disposed on the securing ring, and protruding through the first opening; and a plurality of elastic elements, respectively disposed between the pins and the securing ring, so as to drive the pins to collectively lean against the operation instrument.

* * * * *